US009733187B2

(12) United States Patent
Masilamani et al.

(10) Patent No.: US 9,733,187 B2
(45) Date of Patent: Aug. 15, 2017

(54) METHOD OF DETECTING BLADDER CANCER BY OPTICAL ANALYSIS OF BODILY FLUIDS

(71) Applicant: KING SAUD UNIVERSITY, Riyadh (SA)

(72) Inventors: Vadivel Masilamani, Riyadh (SA);
Mohamad Saleh Alsalhi, Riyadh (SA);
Karim Hamda Farhat, Riyadh (SA);
Danny Monther Rabah, Riyadh (SA);
Saradh Prasad, Riyadh (SA);
Sandhanasamy Devanesan, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 14/641,238

(22) Filed: Mar. 6, 2015

(65) Prior Publication Data

US 2016/0258871 A1    Sep. 8, 2016

(51) Int. Cl.
*G01N 21/03*    (2006.01)
*G01N 21/64*    (2006.01)
*G01N 33/493*   (2006.01)

(52) U.S. Cl.
CPC ......... *G01N 21/6486* (2013.01); *G01N 21/03* (2013.01); *G01N 21/6402* (2013.01); *G01N 33/493* (2013.01); *G01N 2201/06113* (2013.01)

(58) Field of Classification Search
CPC .............. G01N 21/03; G01N 21/6402; G01N 2201/06113; G01N 2021/392;
(Continued)

(56) References Cited

U.S. PATENT DOCUMENTS 5,059,619 A * 10/1991 Haeger et al. ................ 514/410
5,446,157 A *  8/1995 Morgan et al. ................. 546/13
(Continued)

FOREIGN PATENT DOCUMENTS

EP    0 210 351 A2    2/1987
EP    0210351 B1 *   2/1987

OTHER PUBLICATIONS

Silva et al., Enhancement of blood porphyrin emission intensity with aminolevulinic acid administration: A new concept for photodynamic diagnosis of early prostate cancer, Photodiagnosis and Photodynamic Therapy (2011) 8, 7-13.*
(Continued)

*Primary Examiner* — David Porta
*Assistant Examiner* — Djura Malevic
(74) *Attorney, Agent, or Firm* — Richard C. Litman

(57) ABSTRACT

The method of detecting bladder cancer by optical analysis of bodily fluids utilizes optical techniques to determine a concentration of porphyrin in a patient's bodily fluid sample. The patient is administered 5-aminolevulinic acid and, approximately eight hours later, a bodily fluid sample is collected from the patient, and this bodily fluid sample is optically analyzed to measure a concentration of porphyrin therein. Optical analysis is preferably performed by laser-induced fluorescence spectroscopy. If the measured concentration of porphyrin is approximately three times a predetermined porphyrin concentration for a healthy person of the same age as the patient, then the patient is diagnosed with bladder cancer.

8 Claims, 2 Drawing Sheets

(58) Field of Classification Search
CPC ............. G01N 2021/393; G01N 33/50; G01N 33/5005; G01N 33/5008; G01N 2015/0065; G01N 2030/8809; G01N 2030/8813; A61B 5/043; A61B 5/0261; A61B 5/0059; A61B 5/0066; A61B 5/0084; A61B 5/0093; A61B 5/1455; A61B 10/007; A61B 2015/0222; A61B 21/00; A61B 21/359; A61B 21/39; A61B 21/45; A61B 21/6428; A61B 21/6486
USPC .............................................. 250/459.1, 226
See application file for complete search history.

(56) References Cited

U.S. PATENT DOCUMENTS

| | | | |
|---|---|---|---|
| 6,212,425 B1* | 4/2001 | Irion | A61B 1/00186 600/476 |
| 6,335,465 B1* | 1/2002 | Golub | 562/567 |
| 7,067,276 B2* | 6/2006 | Adair | 435/29 |
| 7,247,655 B2 | 7/2007 | Gierskcky et al. | |
| 7,348,361 B2 | 3/2008 | Marti et al. | |
| 7,530,461 B2 | 5/2009 | Gierskcky et al. | |
| 2005/0031541 A1* | 2/2005 | Gierskcky et al. | 424/9.6 |
| 2007/0072825 A1* | 3/2007 | Williams | 514/54 |
| 2008/0058587 A1* | 3/2008 | Boyden | A61B 5/0071 600/104 |
| 2008/0058786 A1* | 3/2008 | Boyden | A61B 5/0071 606/13 |
| 2010/0145416 A1* | 6/2010 | Kang | A61B 5/0059 607/89 |
| 2011/0033386 A1 | 2/2011 | Inoue et al. | |
| 2013/0006116 A1* | 1/2013 | Kim | A61B 5/0059 600/476 |
| 2013/0095520 A1 | 4/2013 | Inoue et al. | |

OTHER PUBLICATIONS

Panjehpour et al., Quantification of Phthalocyanine Concentration in Rat Tissue Using Laser-Induced Fluorescence Spectroscopy, Lasers in Surgery and Medicine 13:23-30 (1993).*
Kriegmair et al., Detection of Early Bladder Cancer by 5-Aminolevulinic Acid Induced Porphyrin Fluorescence, The Journal of Urology vol. 166, 106110, Jan. 1996.*
Inoue et al., Porphyrins as urinary biomarkers forbladder cancer after 5-aminolevulinic acid(ALA) administration: The potential ofphotodynamic screening for tumors, Photodiagnosis and Photodynamic Therapy (2013) 10, 484-489.*
Ogura et al., Tokyo Institute of Technology, Research Report (1) Development of Photodynamic Screening (PDS) of Tumors, ALA and Porphyrin Research Society , ALA-Porphyrin News Letter (May 2013).*
Eker et al. , Clinical Spectral Characterisation of colonic mucosal lesions using autofluorescence and aminolevulinic acid sensition, Gut 1999; 44: pp. 511-518.*
D'Hallewin et al., "Fluorescence Detection of Bladder Cancer; a Review," Eur. Urol., 2002, 42, pp. 417-425.
Grossman, "Improving the Management of Bladder Cancer with Fluorescence Cystoscopy," J. Environ. Pathol. Toxicol. Oncol., 2007, 26, pp. 143-147 (Abstract Only).

* cited by examiner

METHOD OF DETECTING BLADDER CANCER BY OPTICAL ANALYSIS OF BODILY FLUIDS

BACKGROUND OF THE INVENTION

1. Field of the Invention

The present invention relates to the detection and diagnosis of bladder cancer, and particularly to a method of diagnosing bladder cancer in a patient based on optical analysis of a bodily fluid sample collected from the patient.

2. Description of the Related Art

Bladder cancer is any of several types of cancer arising from the epithelial lining (i.e., the urothelium) of the urinary bladder. Cystoscopy is presently the most common diagnostic procedure for bladder cancer. In cystoscopy, a flexible tube bearing a camera and various instruments is introduced into the bladder through the urethra, allowing for both visual diagnosis and biopsying of suspicious lesions. In addition to the invasive nature of cystoscopy, and similar procedures, visual detection of cancerous lesions is not sufficient for establishing pathological classification, cell type or the stage of the present tumor. A so-called "cold cup" biopsy during an ordinary cystoscopy is also not sufficient for pathological staging. Thus, conventional visual detection is typically followed by transurethral surgery. It would be desirable to provide a detection method for bladder cancer which is completely non-invasive, does not require additional surgery, and which is more accurate than visual inspection techniques.

Thus, a method of detecting bladder cancer by optical analysis of bodily fluids solving the aforementioned problems is desired.

SUMMARY OF THE INVENTION

The method of detecting bladder cancer by optical analysis of bodily fluids utilizes optical techniques to determine a concentration of porphyrin in a patient's bodily fluid sample. The patient is administered 5-aminolevulinic acid (also referred to as 8-aminolevulinic acid), which is the first compound in the porphyrin synthesis pathway (i.e., the pathway that leads to heme in mammals). Approximately eight hours later, a bodily fluid sample is collected from the patient, and this bodily fluid sample is optically analyzed to measure a concentration of porphyrin therein. Optical analysis is preferably performed by laser-induced fluorescence spectroscopy. If the measured concentration of porphyrin is approximately three times a pre-determined porphyrin concentration for a healthy person of the same age as the patient, then the patient is diagnosed with bladder cancer with a sensitivity and specificity of approximately 90%.

These and other features of the present invention will become readily apparent upon further review of the following specification.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
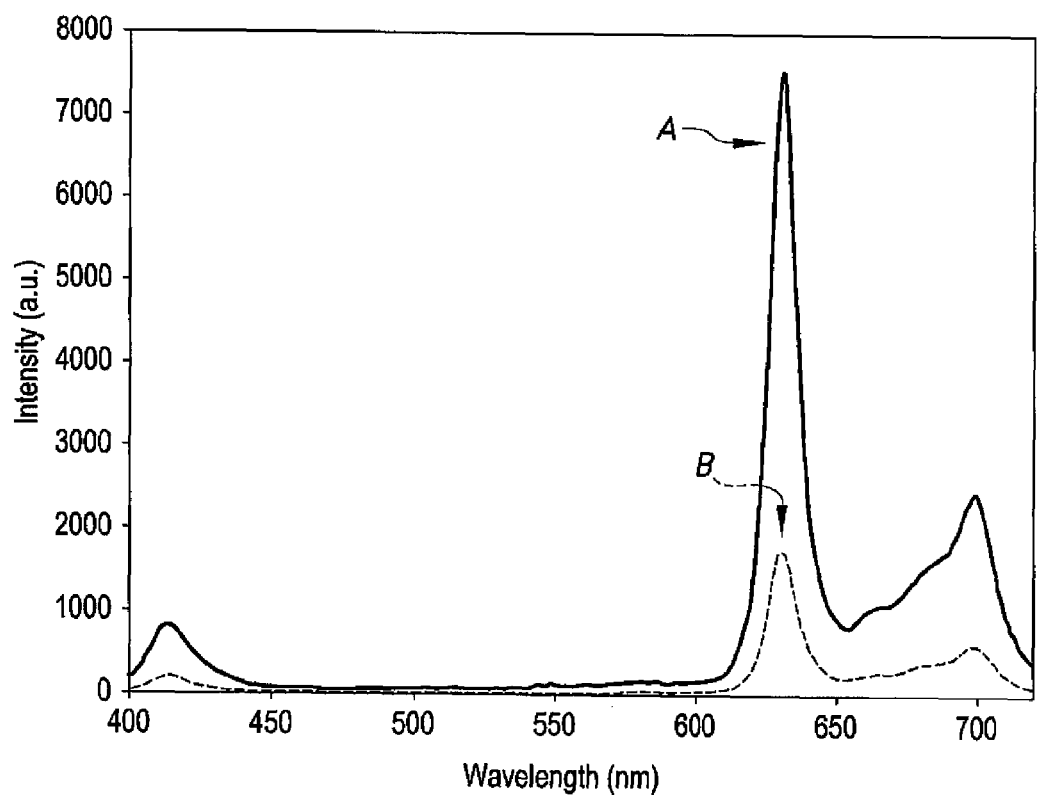
FIG. 1 is a graph illustrating laser-induced fluorescence spectroscopy results for detected porphyrin in a urine sample from a patient known to be suffering from bladder cancer (curve "A") and from a healthy person in the same age group (curve "B").

A method of detecting bladder cancer by optical analysis of bodily fluids utilizes optical techniques to determine a concentration of porphyrin in a patient's bodily fluid sample. The patient is administered 5-aminolevulinic acid (also referred to as 8-aminolevulinic acid), which is the first compound in the porphyrin synthesis pathway (i.e., the pathway that leads to heme in mammals). The 5-aminolevulinic acid is preferably administered orally at a dosage of approximately 5 mg of 5-aminolevulinic acid per kilogram of the patient's body weight. The patient can drink water upon taking the 5-aminolevulinic acid. The patient can wait approximately eight hours before urinating.

Approximately eight hours after oral administration of the 5-aminolevulinic acid, a bodily fluid sample is collected from the patient, and this bodily fluid sample is optically analyzed to measure a concentration of porphyrin therein. Preferably, multiple bodily fluid samples are taken at two hour intervals (i.e., one initial sample at the time of administration, and then subsequent samples taken at two hours, four hours, six hours and eight hours after administration). The bodily fluid being analyzed may be urine and/or blood.

Porphyrin is synthesized by the 5-aminolevulinic acid which is administered to the patient. Porphyrin has a half-life of approximately two hours, thus, after four hours following administration of the 5-aminolevulinic acid, approximately 90% of porphyrin would be eliminated through urine for a healthy person, but would be retained up to eight hours for bladder cancer patients. Blood passing through a cancerous lesion on the bladder would carry an abnormal amount of porphyrin. Thus, the present method can test for this elevated concentration of porphyrin in the blood which directly passes through the cancerous lesion on the bladder (specifically through analysis of the blood plasma). The present method can test for this elevated concentration of porphyrin in the patient's urine, since blood passes through the patient's kidneys and the elevated levels of porphyrin are eliminated (at elevated levels) in the patient's urine.

Approximately 5 mL of the blood and/or urine can be collected. Optical analysis is preferably performed by laser-induced fluorescence spectroscopy, although it should be understood that any suitable type of optical analysis may be performed to determine a concentration of porphyrin in the bodily fluid sample. If the measured concentration of porphyrin is approximately three times a pre-determined porphyrin concentration for a healthy person of the same age as the patient, then the patient is diagnosed with bladder cancer with a sensitivity and specificity of approximately 90%.

In experiments, urine samples were collected in sterile vials, and blood samples were drawn intravenously from the patient. The blood sample was processed via centrifugation and chemical processing to isolate porphyrin in the blood components. Each sample was contained in a four-sided, polished quartz cuvette having dimensions of 1 cm×1 cm×4 cm. The samples were analyzed in a portable laser-induced fluorescence spectrometer. The portable laser-induced fluorescence spectrometer had a power output of 10 mW using a blue diode laser with a wavelength of 405 nm.

The portable laser-induced fluorescence spectrometer was to detect porphyrin concentrations in the samples. In detail, the collimated laser beam was directed on the bodily fluid sample to excite fluorescence from the porphyrin molecules which had been metabolized from the oral administration of 5-aminolevulinic acid. For urine samples in particular, the fluorescence from the urine was detected transversely through a glass lens having a focal length of 10 cm and a diameter of 5 cm. This signal was then dispersed by a diffraction grating having 600 lines/mm. As is conventionally known, the dispersed signal was directed onto a photodiode array, which converted the optical signal into an electrical signal. The electrical signal output was then passed through an amplifier, an analog-to-digital converter and, finally, a digital signal processor, such that the results could be displayed on a computer display.

Figure 2:
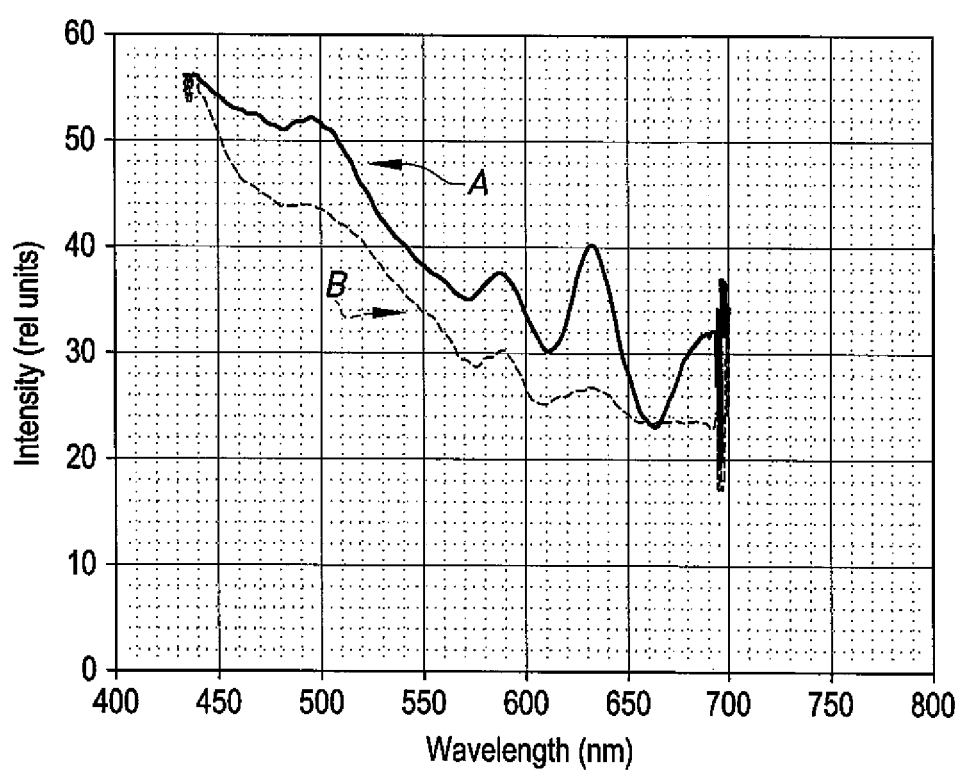
FIG. 2 is a graph illustrating laser-induced fluorescence spectroscopy results for detected porphyrin in a blood plasma sample from a patient known to be suffering from bladder cancer (curve "a") and from a healthy person in the same age group (curve "b").

Following proper calibration and quantification of the signal representing total porphyrin concentration, when the porphyrin intensity was approximately three times greater than that of an age adjusted control, the enhanced, detected concentration was found to be indicative of bladder cancer, with a sensitivity and specificity of 90%. FIG. 1 illustrates the laser-induced fluorescence spectra of urine samples for a patient known to be suffering from bladder cancer (curve "A") and from a healthy person in the same age group as the patient (curve "B"). Both samples were taken approximately eight hours after oral administration of the 5-aminolevulinic acid. As shown, the detected intensity (representing concentration in the urine sample) is significantly greater in curve a, at approximately 630 nm and approximately 680 nm, corresponding to detected porphyrin in the urine samples. Thus, for detected intensities over approximately three times that of the healthy control for porphyrin concentration, one can diagnose bladder cancer in the patient. Similarly, FIG. 2 shows an intensity plot of the laser-induced fluorescence spectra (shown in relative units) for blood plasma samples for a patient known to be suffering from bladder cancer (curve "A") and for a healthy person in the same age group as the patient (curve "B"). Once again, the detected intensity of porphyrin in curve A is significantly greater than that for curve B, indicating that the enhanced concentration of porphyrin in the blood, following administration of the 5-aminolevulinic acid, provides for a diagnosis of bladder cancer in the patient.

It is to be understood that the present invention is not limited to the embodiments described above, but encompasses any and all embodiments within the scope of the following claims.

We claim:

1. A method of detecting bladder cancer in a patient by optical analysis of bodily fluids, comprising the steps of:
orally administering to the patient, approximately 5 mg of 5-aminolevulinic acid per kilogram of the body weight of the patient;
collecting a bodily fluid sample from the patient;
wherein the bodily fluid sample is selected from the group consisting of a urine sample and a blood sample;
performing laser-induced fluorescence spectroscopy on the bodily fluid sample to measure a concentration of porphyrin therein, wherein the laser is a blue diode;
wherein the laser-induced fluorescence spectroscopy including collimating a laser having a power rating about 100 mW, and a wavelength about 405 nm, through the bodily fluid sample, collecting a dispersed laser exiting the bodily fluid sample via a photodiode array, converting into an electrical signal, and amplifying the electrical signal, converting the amplified electrical signal from an analog signal to a digital signal, processing the digital signal with a digital signal processor, and displaying the concentration of porphyrin detected therein; and
diagnosing the patient with bladder cancer if the measured concentration of porphyrin is approximately three times a pre-determined porphyrin concentration for a healthy person of the same age as the patient.

2. The method of detecting bladder cancer by optical analysis of bodily fluids as recited in claim 1, wherein the step of administering the 5-aminolevulinic acid to the patient comprises orally administering the 5-aminolevulinic acid to the patient.

3. The method of detecting bladder cancer by optical analysis of bodily fluids as recited in claim 1, wherein the step of collecting the bodily fluid sample from the patient is performed approximately eight hours after the step of administering the 5-aminolevulinic acid to the patient.

4. A method of detecting bladder cancer by optical analysis of bodily fluids, comprising the steps of:
orally administering 5-aminolevulinic acid to a patient;
wherein the administering includes approximately 5 mg of the 5-aminolevulinic acid per kilogram of the body weight of the patient;
collecting a bodily fluid sample from the patient approximately eight hours after administering the 5-aminolevulinic acid to the patient;
optically analyzing the bodily fluid sample to measure a concentration of porphyrin therein, wherein the laser is a blue diode;
wherein the step of optically analyzing the bodily fluid consists of performing laser-induced fluorescence spectroscopy on the bodily fluid sample to measure a concentration of porphyrin therein;
wherein the laser-induced fluorescence spectroscopy including collimating a laser having a power rating about 100 mW, and a wavelength about 405 nm, through the bodily fluid sample, collecting a dispersed laser exiting the bodily fluid sample via a photodiode array, converting into an electrical signal, and processing the electrical signal to ultimately display the concentration of porphyrin detected therein; and
diagnosing the patient with bladder cancer if the measured concentration of porphyrin is approximately three times a pre-determined porphyrin concentration for a healthy person of the same age as the patient.

5. The method of detecting bladder cancer by optical analysis of bodily fluids as recited in claim 4, wherein the step of administering the 5-aminolevulinic acid to the patient comprises orally administering the 5-aminolevulinic acid to the patient.

6. The method of detecting bladder cancer by optical analysis of bodily fluids as recited in claim 4, wherein the step of collecting the bodily fluid sample from the patient comprises collecting a urine sample from the patient.

7. The method of detecting bladder cancer by optical analysis of bodily fluids as recited in claim 4, wherein the step of collecting the bodily fluid sample from the patient comprises collecting a blood sample from the patient.

8. A method of detecting bladder cancer by optical analysis of bodily fluids, consisting of the steps of:
orally administering approximately 5 mg of 5-aminolevulinic acid per kilogram of body weight of a patient via oral administration;

collecting a bodily fluid sample from the patient approximately eight hours after administering the 5-aminolevulinic acid to the patient;
wherein the bodily fluid sample is chosen from the group consisting of a blood sample and a urine sample, and has a volume on the order of 5 mL;
optically analyzing the bodily fluid sample by performing laser-induced fluorescence spectroscopy on the bodily fluid sample to measure a concentration of porphyrin therein, wherein the laser is a blue diode;
wherein the laser-induced fluorescence spectroscopy including collimating a laser having a power rating about 100 mW, and a wavelength about 405 nm, through the bodily fluid sample, collecting a dispersed laser exiting the bodily fluid sample via a photodiode array, converting into an electrical signal, and processing the electrical signal to ultimately display the concentration of porphyrin detected therein; and
diagnosing the patient with bladder cancer if the measured concentration of porphyrin is approximately three times a pre-determined porphyrin concentration for a healthy person of the same age as the patient.

* * * * *